United States Patent [19]
Giret et al.

[11] Patent Number: 5,858,342
[45] Date of Patent: Jan. 12, 1999

[54] CLEANSING COMPOSITIONS

[75] Inventors: Michel Joseph Marie Giret, Camberley; Chantal Marie Bellemain, Staines, both of Great Britain

[73] Assignee: The Procter & Gamble Company, Cincinnati, Ohio

[21] Appl. No.: 860,774

[22] PCT Filed: Jan. 5, 1996

[86] PCT No.: PCT/US96/00211

§ 371 Date: Jul. 7, 1997

§ 102(e) Date: Jul. 7, 1997

[87] PCT Pub. No.: WO96/20993

PCT Pub. Date: Jul. 11, 1996

[30] Foreign Application Priority Data

Jan. 7, 1995 [GB] United Kingdom ............... 9500313

[51] Int. Cl.$^6$ ................................................. A61K 7/06
[52] U.S. Cl. .................. 424/70.19; 514/784; 514/846
[58] Field of Search .................. 424/70.19; 514/784, 514/846

[56] References Cited

U.S. PATENT DOCUMENTS

| | | | |
|---|---|---|---|
| 4,329,335 | 5/1982 | Su et al. | 424/70 |
| 4,783,282 | 11/1988 | Smid | 252/546 |
| 4,818,440 | 4/1989 | Schäfer | 252/546 |
| 5,409,640 | 4/1995 | Giret et al. | 252/546 |
| 5,494,658 | 2/1996 | Hänel et al. | 424/70.1 |

FOREIGN PATENT DOCUMENTS 0 250181  12/1987  European Pat. Off. .......... C11D 1/94

*Primary Examiner*—Leonard Schenkman
*Attorney, Agent, or Firm*—Darryl C. Little; George W. Allen; T. David Reed

[57] ABSTRACT

A personal cleansing composition comprising:

(a) from about 1% to about 20% by weight of anionic sulphate or sulphonate surfactant;

(b) from about 0.1% to about 10% by weight of carboxymethylated $C_8$–$C_{22}$ alkyl or alkenyl monoethanolamide polyglycol ether;

(c) from about 0.1% to about 10% by Weight of zwitterionic and/or amphoteric surfactants; and (d) from about 0.1% to about 20% by weight of a soluble or dispersible nonionic surfactant selected from ethoxylated animal and vegetable oils and fats and mixtures thereof The cleaning products demonstrate excellent mildness, conditioning benefits, stability, lathering and rinsibility.

29 Claims, No Drawings

CLEANSING COMPOSITIONS

This application is a 371 of PCT/US96/00211 Jan. 5, 1996.

TECHNICAL FIELD

The present invention relates to cleansing compositions. In particular it relates to mild personal cleansing compositions with good skin feel attributes and foaming properties which are suitable for simultaneously cleansing and conditioning the skin and/or the hair and which may be used, for example, in the form of foam bath preparations, shower products, skin cleansers, hand, face and body cleansers, shampoos, intimate washing compositions, etc.

BACKGROUND OF THE INVENTION

Mild cosmetic compositions must satisfy a number of criteria including cleansing power, foaming properties and mildness/low irritancy/good feel with respect to the skin, hair and the ocular mucosae. Skin is made up of several layers of cells which coat and protect the keratin and collagen fibrous proteins that form the skeleton of its structure. The outermost of these layers, referred to as the stratum corneum, is known to be composed of 250 Å protein bundles surrounded by 80 Å thick layers. Hair similarly has a protective outer coating enclosing the hair fibre which is called the cuticle. Anionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the highest shampoo and bar soap standards. Thus, surfactants that are among the mildest are marginal in lather. The use of known high sudsing anionic surfactants with lather boosters, on the other hand, can yield acceptable lather volume and quality but at the expense of clinical skin mildness. These two facts make the surfactant selection, the lather and mildness benefit formulation process a delicate balancing act.

Thus a need exists for personal cleansing products which deliver acceptable in-use skin feel characteristics but which will not dehydrate the skin or result in loss of skin suppleness, which will provide a level of skin conditioning performance in a wash and rinse-off product which previously has only been provided by a separate post-cleansing cosmetic moisturizer and which will produce a foam which is stable and of high quality, which are effective hair and skin cleansers, which have good rinsibility characteristics, and which at the same time have stable product and viscosity characteristics and remain fully stable under long term and stressed temperature storage conditions.

It has now been found that personal cleansing compositions having improved skin feel and moisturisation attributes, both in use and after use, which deliver desirable lathering characterisitcs and good product stability can be formed by the combination of carboxymethylated and suphate or sulphonate surfactants along with zwitterionic and/or amphoteric surfactants and preferably nonionic surfactants. It has also been found that the ratios of carboxymethylated to sulphate/sulphonate surfactant and carboxymethylated to zwitterionic surfactant confer particular benefits in personal cleansing compositions in terms of mildness and lather characteristics.

SUMMARY OF THE INVENTION

The subject of the present invention is a mild, foam-producing, stable cleansing product suitable for personal cleansing of the skin or hair and which may be used as foam bath and shower products, skin cleansers and shampoos etc. According to the present invention, there is provided a liquid personal cleansing composition comprising:

(a) from about 1% to about 20% by weight of anionic sulphate or sulphonate surfactant;

(b) from about 0.1% to about 10% by weight of carboxymethylated $C_8$–$C_{22}$ alkyl or alkenyl monoethanolamide polyglycol ether;

(c) from about 0.1% to about 10% by weight of zwitterionic and/or amphoteric surfactants; and optionally (d) from about 0.1% to about 20% by weight of nonionic surfactant, especially a soluble or dispersible nonionic surfactant selected from ethoxylated animal and vegetable oils and fats and mixtures thereof.

All concentrations and ratios herein are by weight of the cleansing composition, unless otherwise specified. Surfactant chain lengths are also on a weight average chain length basis, unless otherwise specified.

The liquid cleansing compositions herein are based on a combination of anionic with amphoteric and/or zwitterionic surfactants and preferably with nonionic surfactants wherein the anionic surfactant comprises a mixture of carboxymethylated and sulfate or sulphonate surfactants.

Carboxymethylated anionic surfactants preferred for use herein can be generally described as carboxymethylated $C_8$–$C_{22}$ alkyl or alkenyl monoethanolamide polyglycolethers, especially those materials having the general formula (X):

wherein R is $C_8$–$C_{22}$ alkyl or alkenyl, M is H, alkali metal, alkaline earth metal, ammonium or alkanolammonium, and/or ammonium, and x is a number average in the range from about 0.5 to about 15, preferably from about 2 to about 10, for example sodium PEG-6 cocamide carboxylate (a compound of formula X in which x averages about 5). The carboxymethylated anionic surfactant is present in the compositions according to the present invention at a level of from about 0.1% to about 10% by weight. In preferred compositions the level of carboxymethylated surfactant is from about 0.5% to about 8%, more preferably from about 1% to about 5% and especially from about 2% to about 4% by weight of composition. Alkyl or alkenyl chain lengths for the preferred carboxylmethylated surfactants are $C_8$–$C_{18}$, more preferably $C_{12}$–$C_{14}$. The carboxymethylated surfactant is valuable in the compositions according to the present invention for the provision of desirable mildness attributes with the delivery of appropriate lather.

In particularly preferred compositions according to the present invention the weight ratio of carboxymethylated anionic to sulphated or sulphonated anionic surfactant is in the range of from about 1:15 to about 15:1, preferably from about 1:5 to about 5:1, more preferably from about 1:3 to about 3:1.

In addition to the carboxymethylated surfactant the compositions according to the invention contain a mild surfactant system comprising an anionic sulphate or sulphonate together with an amphoteric and/or zwitterionic surfactant and in preferred embodiments, a soluble or dispersible nonionic surfactant. Non-carboxymethylated anionic surfactants other than anionic sulphates and sulphonates can also be present.

The total level of surfactant in the compositions of the invention is preferably from about 5% to about 60%, more preferably from about 6% to about 40%, and especially from about 8% to about 35% by weight. The level of the sulphated or sulphonated anionic surfactant components is in the range from about 1% to about 20%, and especially from about 2% to about 15% by weight of the composition and the level of zwitterionic and/or amphoteric surfactant where present is from about 0.1% to about 10%, preferably from about 1% to about 8%, more preferably from about 1.5% to about 5%. The level of nonionic surfactant, where present, is in the range from about 0.1% to about 20% by weight, preferably from about 0.5% to about 16%, more preferably from about 1% to about 12% by weight. The weight ratio of total anionic surfactant: zwitterionic and/or amphoteric surfactant is in the range from about 1:2 to about 6:1. Other suitable compositions within the scope of the invention comprise mixtures of anionic, zwitterionic and/or amphoteric surfactants with one or more nonionic surfactants. Preferred for use herein are soluble or dispersible nonionic surfactants selected from ethoxylated animal and vegetable oils and fats and mixtures thereof, sometimes referred to herein as "oil-derived" nonionic surfactants.

Mild non-carboxymethylated anionic surfactants suitable for inclusion in the compositions of the invention can generally be described as mild synthetic detergent surfactants and include alkyl and ethoxylated alkyl sulfates, alkyl glyceryl ether sulfonates, methyl acyl taurates, fatty acyl glycinates, N-acyl glutamates, acyl isethionates, alkyl sulfosuccinates, alpha-sulfonated fatty acids, their salts and/or their esters, alkyl ethoxy carboxylates, alkyl phosphate esters, ethoxylated alkyl phosphate esters, acyl sarcosinates and fatty acid/protein condensates, and mixtures thereof. Alkyl and/or acyl chain lengths for these surfactants are $C_8-C_{22}$, preferably $C_{10}-C_{18}$ more preferably $C_{12}-C_{14}$.

Preferred for use herein from the viewpoint of optimum mildness and lathering characteristics are the salts of sulfuric acid esters of the reaction product of 1 mole of a higher fatty alcohol and from about 1 to about 12 moles of ethylene oxide, with sodium and magnesium being the preferred counterions. Particularly preferred are the alkyl sulfates containing from about 2 to 6, preferably 2 to 4 moles of ethylene oxide, such as sodium laureth-2 sulfate, sodium laureth-3 sulfate and magnesium sodium laureth-3.6 sulfate. In preferred embodiments, the sulphated anionic surfactant contains at least about 50%, especially at least about 75% by weight of ethoxylated alkyl sulfate.

The compositions herein can also contain from about 0.1% to about 10%, more preferably from about 0.5% to about 8%, and especially from about 1% to about 5% of a zwitterionic and/or amphoteric surfactant. Zwitterionic and amphoteric surfactants in combination with carboxymethylated anionic surfactants are of particular value in the present compositions for the delivery of good mildness attributes. The preferred ratio of carboxymethylated surfactant to zwitterionic and/or amphoteric surfactant is in the range of from about 5:1 to about 1:5, preferably from about 2:1 to about 1:2.

Zwitterionic surfactants suitable for inclusion in the personal cleansing compositions of the present invention include alkyl betaines of the formula $R_5R_6R_7N^+$ $(CH_2)_n$ $CO_2M(VI)$ and amido betaines of the formula (VII)

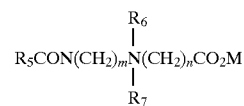

wherein $R_5$ is $C_{12}-C_{22}$ alkyl or alkenyl, $R_6$ and $R_7$ are independently $C_1-C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine.

The compositions for use herein suitably also contain an amphoteric surfactant. Amphoteric surfactants suitable for use in the compositions of the invention include:

(a) imidazolinium surfactants of formula (I)

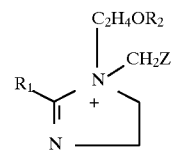

wherein $R_1$ is $C_7-C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (II)

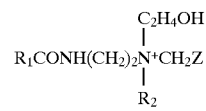

wherein $R_1$, $R_2$ and Z are as defined above;
(b) aminoalkanoates of formula (III)

iminodialkanoates of formula (IV)

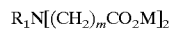

and iminopolyalkanoates of formula (V)

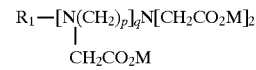

wherein n, m, p, and q are numbers from 1 to 4, and $R^1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula I, although the CTFA Cosmetic Ingredient Dictionary, 3rd Edition indicates the non-cyclic structure II while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula I and/or II in which $R_1$ is $C_8H_{17}$ (especially isocapryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rhone-Poulenc); Alkateric 2CIB. (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals). It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhone-Poulenc.

The compositions of the invention preferably also contain from about 0.1% to about 20%, preferably from about 1% to about 15%, and more preferably from about 2% to about 10% by weight of nonionic surfactant, especially an oil derived nonionic surfactant or mixture of oil derived nonionic surfactants. Oil derived nonionic surfactants are valuable in compositions according to the invention for the provision of skin feel benefits both in use and after use. Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula (VIII)

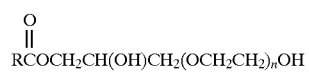

wherein n is from about 5 to about 300, preferably from about 20 to about 250, more preferably from about 30 to about 200, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable oil derived nonionic surfactants of this class are available from Croda Inc. (New York, U.S.A.) under their Crovol line of materials such as Crovol EP40 (PEG 20 evening primrose glyceride), Crovol EP 70 (PEG 60 evening primrose glyceride) Crovol A40 (PEG 20 almond glyceride), Crovol A-70 (PEG 60 almond glyceride), Crovol M40 (PEG 20 maize glyceride), Crovol M-70 (PEG 60 maize glyceride), Crovol PK40 (PEG 12 palm kernel glyceride), and Crovol PK-70 (PEG 45 palm kernel glyceride) and under their Solan range of materials such as Solan E, E50 and X polyethoxylated lanolins and Aqualose L-20 (PEG 24 lanolin alcohol) and Aqualose W15 (PEG 15 lanolin alcohol) available from Westbrook Lanolin. Further suitable surfactants of this class are commercially available from Sherex Chemical Co. (Dublin, Ohio, U.S.A.) under their Varonic Li line of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates). Other oil-derived emollients suitable for use are PEG derivatives of corn, avocado, and babassu oil, as well as Softigen 767 (PEG(6) caprylic/capric glycerides).

Also suitable for use herein are nonionic surfactants derived from composite vegetable fats extracted from the fruit of the Shea Tree (Butyrospermum Karkii Kotschy) and derivatives thereof. This vegetable fat, known as Shea Butter is widely used in Central Africa for a variety of means such as soap making and as a barrier cream, it is marketed by Sederma (78610 Le Perray En Yvelines, France). Particularly suitable are ethoxylated derivatives of Shea butter available from Karlshamn Chemical Co. (Columbos, Ohio, U.S.A.) under their Lipex range of chemicals, such as Lipex 102 E-75 and Lipex 102 E-3 (ethoxylated mono, di-glycerides of Shea butter). Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazlenut oil, olive oil, grapeseed oil, and sunflower seed oil.

Oil derived nonionic surfactants highly preferred for use herein from the viewpoint of optimum mildness and skin feel characteristics are Lipex 102-3 (RTM) (PEG-3 ethoxylated derivatives of Shea Butter) and Softigen 767 (RTM) (PEG-6 caprylic/capric glycerides).

Other nonionic surfactants suitable for use in the compositions of the invention include $C_{12}$–$C_{14}$ fatty acid mono-and diethanolamides, sucrose polyester surfactants and polyhydroxy fatty acid amide surfactants having the general formula (IX).

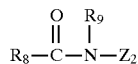

The preferred N-alkyl, N-alkoxy or N-aryloxy, polyhydroxy fatty acid amide surfactants according to formula (IX) are those in which $R_8$ is $C_5$–$C_{31}$ hydrocarbyl, preferably $C_9$–$C_{17}$ hydrocarbyl, including straight-chain and branched chain alkyl and alkenyl, or mixtures thereof and $R_9$ is typically $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH)$—$CH_2OH$, where n is an integer from 1 to 5, inclusive, and R' is H or a cyclic mono- or poly-saccharide, and alkoxylated derivatives thereof. As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a $C_7$–$C_{17}$ straight chain alkyl or alkenyl group.

In compounds of the above formula, $R_8$—CO—N< can be, for example, cocoamide, stearamide, oleamide, lauramide, myristamide, capricamide, palmiamide, tallowamide, etc.

A preferred process for making the above compounds having formula (IX) comprises reacting a fatty acid triglyceride with an N-substituted polyhydroxy amine in the substantial absence of lower ($C_1$–$C_4$) alcoholic solvent, but preferably with an alkoxylated alcohol or alkoxylated alkyl phenol such as NEODOL and using an alkoxide catalyst at temperatures of from about 50° C. to about 140° C. to provide high yields (90–98%) of the desired products.

The compositions according to the present invention may also include a skin conditioning cationic polymer. The cationic polymer is valuable in the compositions according to the present invention for provision of skin feel attributes and for improved rheology and application characteristics in the presence of the hydrophobically modified cellulose ether moiety. The polymeric skin conditioning agent is preferably present at a level from about 0.01% to about 3%, preferably from about 0.04% to about 2% and especially from about 0.05% to about 1% by weight.

Suitable polymers are high molecular weight materials (mass-average molecular weight determined, for instance, by light scattering, being generally from about 2,000 to about 5,000,000, preferably from about 5,000 to about 3,000,000 more preferably from 100,000 to about 1,000,000).

Representative classes of polymers include cationic polysaccharides; cationic homopolymers and copolymers derived from acrylic and/or methacrylic acid; cationic cellulose resins; cationic copolymers of dimethyldiallylammonium chloride and acrylamide and or acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16 (RTM), which contains hydroxypropyl substituents (d.s. of from 0.8–1.1) in addition to the above-specified cationic groups, and quaternized cellulose ethers available commercially under the trade names Ucare Polymer JR-30M, JR-400, Catanal (RTM) and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyidiallylammonium chloride and acrylamide, available commercially under the trade names Merquat 550 and Merquat S, acrylic acid/ dimethyidiallylammonium chloride/acrylamide copolymers available under the trade name Merquat 3300, quaternized vinyl pyrrolidone acrylate or methacrylate copolymers of amino alcohol available commercially under the trade name Gafquat, for example Polyquaternium 11, 23 and 28 (quaternized copolymers of vinyl pyrrolidone and dimethyl aminoethylmethacrylate—Gafquat 755N and HS-100), vinyl pyrrolidone/vinyl imidazolium methochloride copolymers available under the trade names Luviquat HM552, Polyquatemium 2, and polyalkyleneimines such as polyethylenimine and ethoxylated polyethylenimine.

The present compositions can also comprise a nonionic or anionic polymeric thickening component, especially a water-soluble polymeric materials, having a molecular weight greater than about 20,000. By "water-soluble polymer" is meant that the material will form a substantially clear solution in water at a 1% concentration at 25° C. and the material will increase the viscosity of the water. Examples of water-soluble polymers which may desirably be used as an additional thickening component in the present compositions, are hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethyl cellulose, plant exudates such as acacia, ghatti, and tragacanth, seaweed extracts such as sodium alginate, propylene glycol alginate and sodium carrageenan. Preferred as the additional thickeners for the present compositions are natural polysaccharide materials. Examples of such materials are guar gum, locust bean gum, and xanthan gum. Also suitable herein preferred is hydroxyethyl cellulose having a molecular weight of about 700,000.

Additional polymeric thickening agents include acrylic acid/ethyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified crosslinked polymers of acrylic acid having amphipathic properties available under the Trade Name Carbopol 1382, Carbopol 1342 and Pemulen TR-1 (CFTA Designation: Acrylates/10–30 Alkyl Acrylate Crosspolymer). A combination of the polyalkenyl polyether cross-linked acrylic acid polymer and hydrophobically modified cross-linked acrylic acid polymer is also suitable for use herein.

The polymeric thickening component, if present in the compositions of the present invention, is at a level of from 0.01% to 3.0%, preferably from 0.01% to 1.0% by weight.

Further additional thickening agents suitable for use herein include ethylene glycol or polyethylene glycol esters of a fatty acid having from about 16 to about 22 carbon atoms and up to 7 ethyleneoxy units, preferably the ethylene glycol stearates, both mono and distearate, but particularly the distearate containing less than about 7% of the mono stearate, alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide, alkyl ($C_{16}$–$C_{22}$) dimethyl amine oxides such as stearyl dimethyl amine oxide and electrolytes such as magnesium sulphate and sodium chloride salts.

The viscosity of the final composition (Brookfield DCP, Spindle S41, 1 rpm, 26.7° C., neat) is preferably at least about 200 cps, more preferably from about 400 to about 10,000 cps, especially from about 500 to about 4,000 cps, more especially from about 500 to about 2,000 cps.

The cleansing compositions can optionally include other hair or skin moisturizers which are soluble in the cleansing composition matrix. The preferred level of such moisturizers is from about 0.5% to about 20% by weight. In preferred embodiments, the moisturizer is selected from essential amino acid compounds found naturally occurring in the stratum corneum of the skin and water-soluble nonpolyol nonocclusives and mixtures thereof.

Some examples of more preferred nonocclusive moisturizers are polybutene, squalane, sodium pyrrolidone carboxylic acid, lactic acid, L-proline, guanidine, pyrrolidone, hydrolyzed protein and other collagen-derived proteins, aloe vera gel, acetamide MEA and LMEA and mixtures thereof.

Compositions according to the present invention may also include an opacifier or pearlescing agent. Such materials may be included at a level of from about 0.01% to about 5%, preferably from about 0.2% to about 1.3% by weight. A suitable opacifier for inclusion in the present compositions is a polystyrene dispersion available under the trade names Lytron 621 & 631 (RTM) from Morton International. Additional opacifiers/pearlescers suitable for inclusion in the compositions of the present invention include: titanium dioxide, $TiO_2$; EUPERLAN 810 (RTM); TEGO-PEARL (RTM); long chain ($C_{16}$–$C_{22}$) acyl derivatives such as glycol or polyethylene glycol esters of fatty acid having from about 16 to about 22 carbon atoms and up to 7 ethyleneoxy units; alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide and alkyl ($C_{16}$–$C_{22}$) dimethyl amine oxides such as stearyl dimethyl amine oxide.

In preferred compositions the opacifier/pearlescer is present in the form of crystals. In highly preferred compositions the opacifier/pearlescer is a particulate polystyrene dispersion having a particle size of from about 0.05 microns to about 0.45 microns, preferably from about 0.17 microns to about 0.3 microns, such dispersions being preferred from the viewpoint of providing optimum rheology and shear-thinning behaviour. Highly preferred is styrene PVP copolymer and Lyton 631 (RTM).

A number of additional optional materials can be added to the cleansing compositions each at a level of from about 0.1% to about 2% by weight. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxyethanol; other moisturizing agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., U.S.A. and described in U.S. Pat. No. 4,076,663; solvents; anti-bacterial agents such as Oxeco (phenoxy isopropanol) and Triclosan; low temperature phase modifiers such as ammonium ion sources (e.g. $NH_4$ Cl); viscosity control agents such as magnesium sulfate and other electrolytes; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. Water is also present at a level preferably of from about 30% to about 94.99%, preferably from about 40% to about 90%, more preferably at least about 60% by weight of the compositions herein.

The pH of the compositions is preferably from about 4 to about 10, more preferably from about 6 to about 9, especially from about 5 to about 6.

The invention is illustrated by the following non-limiting examples.

In the examples, all concentrations are on a 100% active basis and the abbreviations have the following designation:

Amphoteric 1 Cocoamphodiacetate

Amphoteric 2 Cocoamidopropyl betaine

Anionic 1 Sodium laureth-3 sulfate

Anionic 2 Sodium PEG-6 Cocamide Carboxylate

Nonionic PEG-80 Glyceryl Tallowate

Crovol Crovol EP 70 (PEG 60 evening primrose triglycerides)

GA Polyhydroxy fatty acid amide of formula IX in which $R_8$ is $C_{11}$–$C_{17}$ alkyl, $R_9$ is methyl, and $Z_2$ is $CH_2(CHOH)_4CH_2OH$ Polymer 1 Polymer JR-30(RTM)—hydroxyethylcellulose reacted with epichlorohydrin and quaternized with trimethylamine, m.wt. $4\times10^6$ Polymer 2 Gafquat 755N Preservative Phenoxyethanol/sodium benzoate/EDTA (4:2:1)

Pearlescer Ethyleneglycoldistearate/emulsifier mixture

Opacifier Lytron 631 (RTM)
Oil Soyabean Oil
Softigen 767 PEG(6) caprylic/capric glycerides

EXAMPLES I TO VI

The following are personal cleansing compositions in the form of shower gel or bath foam products and which are representative of the present invention:

|  | I | II | III | IV | V | VI |
|---|---|---|---|---|---|---|
| Amphoteric 1 | — | — | 2.0 | — | 3.5 | — |
| Amphoteric 2 | 2.0 | 3.0 | — | 5.0 | — | 4.0 |
| Anionic 1 | 6.0 | 6.0 | 2.0 | 8.0 | 6.0 | 4.0 |
| Anionic 2 | 6.0 | 2.0 | 6.0 | 4.0 | 1.0 | 3.0 |
| GA | — | — | — | — | 3.0 | — |
| Softigen 767 | — | 1.0 | — | 2.0 | 2.0 | — |
| Nonionic | 2.0 | 2.0 | 3.0 | 3.0 | 2.0 | — |
| Crovol | — | — | 1.0 | — | — | 3.0 |
| Polymer 1 | 0.1 | 0.2 | — | 0.2 | 0.1 | — |
| Polymer 2 | — | — | 0.5 | — | — | 0.2 |
| Glycerine | 1.0 | 3.0 | — | 2.0 | — | 5.0 |
| Pearlescer | — | — | — | 3.0 | 1.0 | 1.0 |
| Opacifier | 0.2 | 0.3 | 0.4 | — | — | — |
| Preservative | 0.5 | 0.5 | 0.5 | 1.0 | 1.0 | 1.0 |
| Perfume | 0.5 | | | | | |
| Water | to 100 | | | | | |

Compositions I to VI are prepared by firstly dispersing the water-soluble or colloidally water-soluble polymeric rheology modifier in water at 25° C. either in a Tri-blender (RTM) or by extended stirring prior to neutralisation with NaOH or alternative base mixture and hydration. In examples II, IV and VI the mixture can be heated to about 50° C. to enhance dispersion efficiency. Next, the surfactants and other skin care agents are added along with the remaining water-soluble, oil-insoluble ingredients. Finally the remaining water, preservative, opacifier and perfume are added.

The products provide excellent in-use and efficacy benefits including mildness, skin conditioning, skin moisturising, good lather characterisitcs, stability, cleansing and rinsibility.

What is claimed is:

1. A personal cleansing composition comprising:

(a) from about 1% to about 20% by weight of anionic sulphate or sulphonate surfactant:

(b) from about 0.1% to about 10% by weight of carboxymethylated $C_8$–$C_{22}$ alkyl or alkenyl monoethanolamide polyglycol ether;

(c) from about 0.1% to about 10% by weight of zwitterionic, and/or amphoteric surfactants; and (d) from about 0.1% to about 20% by weight of a soluble or dispersible nonionic surfactant selected from the group consisting of ethoxylated mono-glycerides; ethoxylated di-glycerides, ethoxylated tri-glycerides; ethoxylated butters; ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppy seed oil, pine oil, castor oil, soybean oil, avocado oil, safflower oil, coconut oil, hazelnut oil, olive oil, grapeseed oil, and sunflower seed oil; and mixtures thereof.

2. A composition according to claim 1 wherein the composition has a viscosity (Brookfield DCP, Spindle S41, 1 rpm, 26.7° C., neat) in the range from 500 to 2,000 cps.

3. A composition according to claim 1 wherein the oil derived nonionic surfactant comprises one or more ethoxylated oil or fat having the formula (V)

$$RCOCH_2CH(OH)CH_2(OCH_2CH_2)_nOH$$

wherein n is from about 5 to about 300, and wherein R comprises an aliphatic radical having an average from about 5 to 20 carbon atoms.

4. A composition according to claim 3 wherein in formula (V) n is from about 20 to about 250.

5. A composition according to claim 4 wherein in formula (V) n is from about 30 to about 200.

6. A composition according to claim 5 wherein in formula (V) R comprises an aliphatic radical having an average from about 9 to 20 carbon atoms.

7. A composition according to claim 6 wherein in formula (V) R comprises an aliphatic radical having an average from about 11 to 18 carbon atoms.

8. A composition according to claim 7 wherein in formula (V) R comprises an aliphatic radical having an average from about 12 to 16 carbon atoms.

9. A composition according to claim 1 comprising from about 2% to about 16%, by weight of the oil derived nonionic surfactant.

10. A composition according to claim 9 comprising from about 3% to about 12% by weight of the oil derived nonionic surfactant.

11. A composition according to claim 1 wherein the carboxymethylated anionic is present at a level of from about 0.5% to about 8% by weight of composition.

12. A composition according to claim 11 wherein the carboxymethylated anionic is present at a level of from about 1% to about 5% by weight of composition.

13. A composition according to claim 1 wherein the carboxymethylated anionic is a $C_{12}$–$C_{14}$ alkyl monoethanolamide polyglycol ether.

14. A composition according to claim 1 wherein the ratio of carboxymethylated anionic to anionic sulphate or sulphonate is in the range of from about 1:15 to about 15:1.

15. A composition according to claim 14 wherein the ratio of carboxymethylated anionic to anionic sulphate or sulphonate is in the range of from about 1:5 to about 5:1.

16. A composition according to claim 1 comprising a mixture of anionic with zwitterionic and/or amphoteric surfactants and soluble or dispersible nonionic surfactants.

17. A composition according to claim 1 comprising from about 1% to about 20% by weight of anionic sulphate or sulphonate.

18. A composition according to claim 17 comprising from about 2% to about 15% by weight of anionic sulphate or sulphonate.

19. A composition according to claim 1 wherein the anionic sulphate or sulphonate surfactant is selected from the group consisting of ethoxylated alkyl sulfates, alkyl glyceryl ether sulfonates, acyl isethionates, alkyl sulfosuccinates, alpha-sulfonated fatty acids, their salts and/or their esters, and mixtures thereof.

20. A composition according to any of claim 1 wherein the anionic sulphate or sulphonate comprises an ethoxylated $C_8$–$C_{22}$ alkyl sulfate.

21. A composition according to claim 1 wherein the amphoteric surfactant is selected from the group consisting of:

(a) imidazolinium derivatives of formula (I)

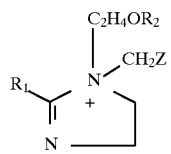

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (II)

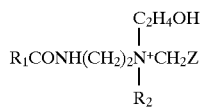

wherein $R_1$, $R_2$ and Z are as defined above:
(b) aminoalkanoates of formula (III)

and iminodialkanoates of formula (IV)

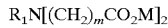

wherein n and m are numbers from 1 to 4, and $R_1$ and M are independently selected from the groups specified in (a) above; and
(c) mixtures thereof.

22. A composition according to claim 21 wherein the amphoteric is selected from the group consisting of the imidazolinium derivatives of formula I and/or ammonium derivatives of formula II.

23. A composition according to claim 1 wherein the weight ratio of total anionic surfactant:zwitterionic and/or amphoteric surfactant is in the range from about 1:2 to about 6:1.

24. A composition according to claim 1 wherein the anionic surfactant, zwitterionic and/or amphoteric surfactant together comprise from about 8% to about 35%, by weight of the composition.

25. A composition according to claim 24 wherein the anionic surfactant, zwitterionic and/or amphoteric surfactant together comprise from about 10% to about 30% by weight of the composition.

26. A composition according to claim 1 additionally comprising from 0.01% to 3%, of a cationic or nonionic polymeric skin or hair conditioning agent, selected from the group consisting of cationic and nonionic polysaccharides; cationic and nonionic homopolymers and copolymers derived from acrylic and/or methacrylic acid, cationic and nonionic cellulose resins; cationic copolymers of dimethyidiallylammonium chloride and acrylic acid; cationic homopolymers of dimethyldiallylammonium chloride; cationic polyalkylene and ethoxypolyalkylene imines; quaternized silicones, and mixtures thereof.

27. A composition according to claim 26 additionally comprising from about 0.04% to about 2% of a cationic or nonionic polymeric skin or hair conditioning agent, selected from the group consisting of cationic and nonionic polysaccharides, cationic and nonionic homopolymers and copolymers derived from acrylic and/or methacrylic acid, cationic and nonionic cellulose resins; cationic copolymers of dimethyldiallylammonium chloride and acrylic acid; cationic homopolymers of dimethyldiallylammonium chloride; cationic polyalkylene and ethoxypolyalkylene imines; quaternized silicones, and mixtures thereof.

28. A composition according to claim 27 additionally comprising from about 0.05% to 1% of a cationic or nonionic polymeric skin or hair conditioning agent, selected from the group consisting of cationic and nonionic polysaccharides, cationic and nonionic homopolymers and copolymers derived from acrylic and/or methacrylic acid, cationic and nonionic cellulose resins; cationic copolymers of dimethyldiallylammonium chloride and acrylic acid; cationic homopolymers of dimethyldiallylammonium chloride; cationic polyalkylene and ethoxypolyalkylene imines; quaternized silicones, and mixtures thereof.

29. A composition according to claim 1 additionally comprising moisturiser selected from the group consisting of glycerin, polyethylene glycol, propylene glycol, sorbitol, polyethylene glycol and polypropylene glycol ethers of methyl glucose, sodium pyrrolidone carboxylic acid, lactic acid, L-proline and mixtures thereof.

* * * * *